United States Patent
Thomsen

(10) Patent No.: US 9,212,993 B2
(45) Date of Patent: Dec. 15, 2015

(54) DETERMINATION OF SULPHUR DIOXIDE IN A LIQUID

(75) Inventor: Henrik Thomsen, Valby (DK)

(73) Assignee: FOSS ANALYTICAL A/S, Hilleroed (DK)

(*) Notice: Subject to any disclaimer, the term of this patent is extended or adjusted under 35 U.S.C. 154(b) by 0 days.

(21) Appl. No.: 13/884,811

(22) PCT Filed: Nov. 30, 2010

(86) PCT No.: PCT/EP2010/068483
§ 371 (c)(1),
(2), (4) Date: May 10, 2013

(87) PCT Pub. No.: WO2012/072106
PCT Pub. Date: Jun. 7, 2012

(65) Prior Publication Data
US 2013/0236976 A1 Sep. 12, 2013

(51) Int. Cl.
*G01N 21/59* (2006.01)
*G01N 21/3504* (2014.01)
(Continued)

(52) U.S. Cl.
CPC ............ *G01N 21/59* (2013.01); *G01N 21/3504* (2013.01); *G01N 33/0042* (2013.01); *G01N 33/146* (2013.01)

(58) Field of Classification Search
CPC . G01N 21/3504; G01N 21/59; G01N 33/146; G01N 33/0042
USPC ........ 436/20, 501; 422/82.05, 69, 82.01, 547; 702/24
See application file for complete search history.

(56) References Cited

U.S. PATENT DOCUMENTS

| 5,844,123 A | 12/1998 | Marsh et al. |
| 2003/0178323 A1 | 9/2003 | Fiedler et al. |

(Continued)

FOREIGN PATENT DOCUMENTS

| DE | 102009013534 A1 | 9/2010 |
| EP | 1308713 A1 | 5/2003 |

(Continued)

OTHER PUBLICATIONS

Cmelik, J. et al. "Determination of free and total sulfur dioxide in wine samples by vapour-generation inductively coupled plasma-optical-emission spectrometry". Analytical and Bioanalytical Chemistry; Jul. 2005.

(Continued)

*Primary Examiner* — Rebecca M Fritchman
(74) *Attorney, Agent, or Firm* — Harness, Dickey & Pierce, P.L.C.

(57) ABSTRACT

A system for the measurement of free and bound SO2 in a liquid beverage product sample comprising a sample container having a volume sufficient to provide a headspace above the sample into which a gas can pass; a gas flow system adapted to extract gas from the headspace and recirculating it back into the liquid volume; a measurement system configured to monitor a time dependent evolution of SO2 in gas from the gas flow system; and a dosing apparatus fluidly connected to the container to supply an hydrolysis reagent thereto. A heater unit is provided for supplying thermal radiation into the container to elevate the temperature of sample therein sufficient to facilitate the hydrolysis reaction and a signal processor operates to deconvolute the monitored evolution to generate an indication of the concentration of each of the free SO2 and the total SO2 content of the sample.

8 Claims, 3 Drawing Sheets

(51) Int. Cl.
  *G01N 33/00* (2006.01)
  *G01N 33/14* (2006.01)
  *G01N 21/00* (2006.01)

(56) References Cited

U.S. PATENT DOCUMENTS

2012/0015449 A1* 1/2012 Fiedler .................... 436/501
2012/0122132 A1* 5/2012 Kim ........................ 435/18

FOREIGN PATENT DOCUMENTS

| EP | 1840557 A1 | 10/2007 |
| WO | WO-99/53312 A1 | 10/1999 |
| WO | WO-2008/025085 A1 | 3/2008 |
| WO | WO-2010/105650 A2 | 9/2010 |

OTHER PUBLICATIONS

Sato, M. et al. "Varietal Differences in the Phenolic Content and Superoxide Radical Scavenging Potential of Wines from Different Sources". Journal of Agricultural and Food Chemistry; Jan. 1996; XP002040576.

International Search Report PCT/ISA/210 for PCT/EP2010/068483 dated Jun. 15, 2011.

Written Opinion PCT/ISA/237 for PCT/EP2010/068483 dated Jun. 15, 2011.

Chilean Office Action issued in Chilean Patent Application No. 2013-001079, dated Mar. 9, 2015.

"*Compendium of International Methods of Analysis-OIV*", Edition 2011, vol. 2.

* cited by examiner

DETERMINATION OF SULPHUR DIOXIDE IN A LIQUID

BACKGROUND

This application is the national phase under 35 U.S.C. §371 of PCT International Application No. PCT/EP2010/068483 which has an International filing date of Nov. 30, 2010.

FIELD

The present invention relates to the determination of sulphur dioxide ($SO_2$) in a liquid. Particularly the present invention relates to the determination of both free and total $SO_2$ in a liquid, most particularly a beverage product such as wine, beer or juice or must, other vinification products or intermediates of the beverage production process.

DESCRIPTION OF THE RELATED ART

It is well known that the presence and/or in particular the amount of free $SO_2$ and other components of interest in a beverage product or an intermediate product of the beverage production process may be determined by the optical analysis of headspace gases above a liquid sample. By measuring the presence in the gas of species indicative of the one or more component of interest in the liquid (perhaps being one and the same) then the presence and/or particularly the amount of that component can be readily determined.

It is known, from for example EP 1 308 713, to determine components of a liquid sample by optical analysis of a headspace gas that is allowed to become established in a sealed sample container having a volume greater than that of the liquid sample. This document discloses in particular a method for the analysis of free $SO_2$ in wine or other beverage by use of infrared measurement instrumentation. According to this method a liquid sample of a specific volumetric size is introduced into a sealed container having a fluid holding volume in excess of the specific volumetric size. Carbon dioxide ($CO_2$) and other gases that may interfere with the measurement are first removed from the headspace gases. Thereafter a concentration of free $SO_2$ is allowed to establish in the gaseous headspace. A gas sample is then removed from the headspace and the concentration of free $SO_2$ in that gas sample is measured by means of the infrared measurement instrumentation adapted to measure the attenuation of infrared radiation transmitted through the sample. From this measurement the content of free $SO_2$ in the beverage is determined.

EP 1 840 557 discloses an apparatus for detecting free SO2 from a liquid, typically wine, sample and comprises measurement instrumentation adapted to detect free SO2 by one or both of a quantitative and a qualitative measurement of absorption of optical radiation by gas extracted from a headspace above the liquid sample. A gas flow system is configured to remove gas from and to recirculate extracted gas to the headspace through the liquid sample in order to speed up the extraction of SO2. A dosing device (8) may also be provided for transfer of a reagent, typically an acid, from a reservoir into the liquid to effect release into the liquid of a species indicative of the component of interest for extraction into the headspace by the recirculated gas.

It is often important in beverage production, winemaking for example, that both free and total $SO_2$ content is known. Standard reference methods such as described in the publication "Compendium of International Methods of Analysis-OIV", Edition 2011 Vol. 2, References MA-AS323-04A, B and C, disclose that free and total $SO_2$ content are to be determined in two separate measurements. Free $SO_2$ is to be determined at room temperature or lower but typically at room temperature using acid hydrolysis, whereas total $SO_2$ is to be determined at significantly elevated temperatures, typically around 100° C., again using acid hydrolysis. Typically for each of the free and the bound determinations around 15 mL (milliliters) of phosphoric acid is added to 50 mL of sample liquid and $SO_2$ is extracted over a 15 minute period.

SUMMARY

According to a first aspect of the present invention there is provided a method of determining both free and total $SO_2$ in a liquid beverage product sample comprising performing hydrolysis of the liquid sample at an elevated temperature; monitoring a temporal evolution of $SO_2$ in headspace gas during hydrolysis to establish a time dependent concentration variation; and deconvoluting the time dependent concentration variation, for example by using a suitably constructed calibration, such as a multivariate calibration, that links the temporal changes in $SO_2$ evolution with the amounts of $SO_2$ and to determine using this an indication of each of the free and total $SO_2$ content of the liquid sample. This enables both free and total $SO_2$ to be determined from a single chemical hydrolysis reaction. Moreover, as the evolution of $SO_2$ is monitored during the hydrolysis and before steady-state is reached then the method is relatively rapid since equilibrium (typically 15 minutes for the reference method) is not required.

Usefully, monitoring the evolution involves detecting at a plurality of times during hydrolysis wavelength dependent absorbance values of the headspace gas at one or more wavelengths, for example in the infrared region, responsive to changes in $SO_2$.

In an embodiment there is provided an additional step of re-circulating the headspace gas through the liquid sample at least once during monitoring the evolution of $SO_2$. This enhances the extraction of $SO_2$ from the liquid sample to thereby speed up the determinations of free and total $SO_2$.

According to a second aspect of the present invention there is provided a measurement system for measurement, preferably optical, most preferably infrared, measurement of each if free and bound $SO_2$ in a liquid beverage product sample which system is adapted to operate to perform the method according to the first aspect of the present invention and hence has the advantages associated with the first aspect.

BRIEF DESCRIPTION OF THE DRAWINGS

These and other advantages will become apparent from a reading of the following description of exemplary embodiments of the system according to the second aspect of the present invention adapted to operate according to the method of the first aspect. This description is made with reference to the drawings of the accompanying figures, where.

DETAILED DESCRIPTION

Figure 1:
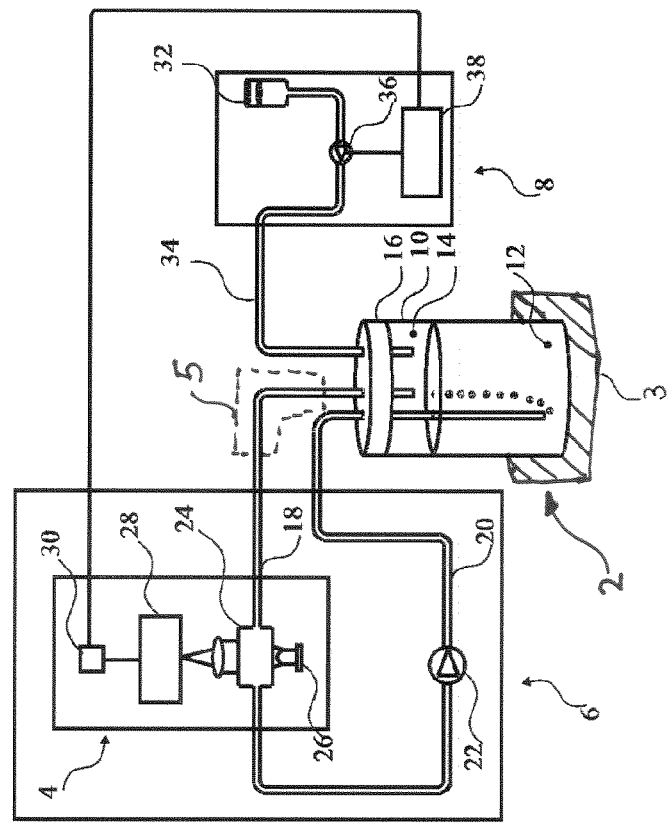
FIG. 1 shows schematically an embodiment of a system according to the present invention configured for $SO_2$ determination in a beverage.

Considering now the exemplary system which is illustrated schematically in FIG. 1. Although this will be described in connection with the determination of an amount of $SO_2$ in a beverage, such as wine, cider, beer or fruit juice, or an intermediate product of the beverage production process it is not intended that the present invention is limited only to this application.

As illustrated, the system of FIG. 1 can be considered to comprise four functional elements: a sample holder 2; optical measurement instrumentation 4; a gas flow system 6; and dosing apparatus 8.

The sample holder 2 of the present embodiment comprises a liquid container 10 which is dimensioned to define an inner volume greater than an expected predetermined volume of a liquid sample (wine say) 12 which will, in use, be transferred into and retained by the container 10. This permits the formation of a gas containing headspace volume 14 in the container 10 above the liquid 12. The sample holder 2 additionally comprises a heater unit 3 which operates to elevate the temperature of the sample in the container 10 sufficiently for an hydrolysis reaction to occur. The temperature of course depends both on the sample and on the reagent but typically is above 60° C. and is often around boiling point of the sample/reagent mixture. A thermocouple may be included (not shown) in operable connection with a temperature control unit, such as a known PID type controller, of the heater unit 3 in order to maintain the temperature of the liquid 12 at a known and fixed temperature. The signal processor 30 may include a component known to the art which will operate as the temperature control unit. The sample holder 2 here further comprises a preferably removable closure 16 to seal the container 10 against unintentional egress of fluid, in particular gas. According to alternative embodiments the container 10 may, for example, comprise a sealed end user container, such as a corked bottle, a can or waxed paper container, and appropriate fluid connections established by piercing the container 10 or the container 10 may comprise a single-use container.

The gas flow system 6 is provided in gas communication with the inner volume of the container 10, here via the closure 16 such that gas from the headspace volume 14 may be extracted from and returned to the container 10. The gas flow system 6 of the present embodiment comprises an extraction conduit portion 18, coupled to the headspace volume 14, and a return conduit portion 20, coupled to the inner volume of container 10 at a location such that in use gas from the conduit 20 is supplied in to the liquid sample 12. A circulation pump 22 is operably connected to the gas flow circuit 6 to effect recirculation of gas from the head space 14 to the liquid 12 via the extraction 18 and the return 20 conduit portions. The circulation pump 22 may be considered as delimiting these extraction and return conduit portions 18, 20 which are respectively located upstream and downstream the pump 22. In one embodiment a cooling device 5 may be included to cool the gas in the extraction conduit portion 18 before it is analysed by the measurement instrumentation 4. In this manner condensation of the headspace gas in the measurement instrumentation 4 may be avoided.

The optical measurement instrumentation 4 is disposed to receive gas from gas flow system 6 and is provided with a measurement station 24 at which the interaction of optical radiation with the gas is monitored. In the present embodiment the measurement station 24 is defined by a cuvette which is connected in-line to the gas flow circuit of the flow system 6. Alternatively the measurement station 24 may, for example, comprise a suitably optically transparent region of the extraction or supply gas conduit portions 18, 20. The instrumentation 4 comprises complementary optical radiation supply 26 and detection element 28 cooperable to monitor absorption of optical radiation from the supply 26 by gas from the headspace 14. As $SO_2$ has a known absorption peak in the wavelength region around 1380 $cm^{-1}$ then the optical radiation supply 26 may suitably comprise infrared radiation supply, emitting in the appropriate wavelength region. It is also known that for wine and other alcoholic beverages ethanol also contributes to absorption in that region and that ethanol itself has an absorption peak at around 1250 $cm^{-1}$. The optical radiation supply 26 may therefore usefully be configured to generate infrared radiation containing radiation at these two absorption wavelengths, such as for example generating throughout the wavelength region between 1000 $cm^{-1}$ and 1900 $cm^{-1}$ or alternatively in a narrow band around 1250 $cm^{-1}$ and one around 1380 $cm^{-1}$.

The detection element 28 may comprise a conventional Fourier Transform Infra-Red (FTIR) spectrometer configured to operate in a known manner and disposed to detect optical radiation from the supply 26 after its interaction with gas in the cuvette 24. In the present embodiment the FTIR spectrometer 28 and the supply 26 are mutually arranged to operate in transmission mode, which is a mode where radiation is transmitted through the cuvette 24 from the supply 26 to be detected by the spectrometer 28.

According to alternative embodiments these supply 26 and detection 28 elements may be configured to operate in known reflectance or transflectance modes. Indeed, the FTIR spectrometer may be substituted for other known detection elements, such as a fixed or a scanning dispersion element monochromator or a detector and filter configuration, suitable for monitoring absorption of optical radiation by a species in the gas which is indicative of the presence of $SO_2$ in the liquid sample 12 (here wine). Indeed other known $SO_2$ sensors, for example an electronic or electrochemical cell type sensor, may be substituted which are not dependent on optical absorption in the gas for monitoring the $SO_2$ content.

In a further embodiment the absorption of infrared radiation by the liquid sample is also monitored, for example so as to be able to determine in a known manner the alcohol and/or sugar content of the sample or other components of the sample. The optical radiation supply 26 may, in this further embodiment, be diverted, for example by means of a beam splitter or an optical switch, to also illuminate the sample in the container 10 and light supplied to the detection element 28 after passing through the liquid sample. Light conduits, such as suitable optical fibers (not shown) may be provided to lead the infrared illumination to and from the liquid sample 12 in the container 10.

A signal processor 30, here shown as integral with the optical measurement instrumentation 4, is connected to receive an output from the FTIR spectrometer 28 which is representative of wavelength correlated intensities of detected optical radiation and to analyse the received output signal to establish at least a quantitative measure of at least $SO_2$ in the gas (also components of interest in the liquid sample in an alternative embodiment outlined above) in a manner known in the art. For example the signal processor 30 may be provided with, or have access to via a telecommunications link, a calibration such as a multivariate calibration, that links the wavelength correlated intensities to the concentration of $SO_2$ (or components in the liquid) present in the gas. It will be appreciated that the signal processor 30 may have one or more separate components cooperatively connected by a wired link or a telecommunications link so as to achieve the desired functionality.

The dosing apparatus 8 comprises a reagent reservoir 32 which is fluidly connectable to the inner volume of the container 10 via a conduit 34; a dosing pump 36 for effecting the transfer of reagent from the reservoir 32 to the container 10; and a controller 38 for controlling the operation of the pump 36. The controller 38 is connected to the signal processor 30 to receive the control signal and to trigger the operation of the pump 36 in dependence thereof.

In the present embodiment the reagent is an acid which when added to the wine adjusts the pH of the liquid to cause, when heated sufficiently, the liberation into the wine of the otherwise bound $SO_2$. This liberated $SO_2$ is then available to be extracted from the wine and in to the headspace volume 14 by the recirculated headspace gas being passed through the wine sample 12 from the flow system 6. In this manner a gas may be rapidly generated in the headspace 14 that is enriched with $SO_2$.

In an exemplary operation the liquid sample, here approximately 2 ml of wine or must, and the acid reagent, here for example 1 ml of 25% Phosphoric acid, are sequentially pumped in to the container 10. A very small amount of antifoaming agent (e.g. silicone oil) may be added to the acid before pumping in order to avoid foaming. This provides the advantage that the amount of reagent to be employed is much less than that employed with the reference methods although the same chemistry as the reference method is employed. The container 10 is constantly heated, here to around 85° C., to facilitate the acid hydrolysis. The mixture is continuously bubbled through by the re-circulating gas system 6 and the recirculated headspace gas presented to the cuvette 24. The free $SO_2$ is almost instant liberated from the liquid into equilibrium with the gas phase. Slowly the bound $SO_2$ is hydrolyzed and also released into equilibrium with the gas phase. This hydrolysis is allowed for between around 30 sec to around 4 minutes depending on the accuracy of determination that is wanted. Even after 4 minutes the hydrolysis is not necessarily completed to a steady-state but still enables accurate determinations to be made in much less time than with the reference methods. At a plurality of times during the hydrolysis reaction and before steady-state infrared absorbance spectra of the gas are collected by the measurement instrumentation 4. On the basis of the infrared absorbance spectra collected the evolution of the $SO_2$ concentration in the gas cell over time can be deducted within the signal processor 30 by, for example CLS (classical least square), PLS (partial least squares) or other multivariate analysis calibration. According to an embodiment of the method of the present invention both the free and bound $SO_2$ concentrations in the sample can then be deducted from a deconvolution of the time curve of the $SO_2$ concentration in the gas cell. The total $SO_2$ can also be calculated since the total is a sum of free and bound. The free $SO_2$ content in the sample is correlated to the fast release of $SO_2$ concentration in the cuvette 24. The bound $SO_2$ is correlated to the rate of release (slope) of the $SO_2$ after the free $SO_2$ has been liberated.

This deduction may be improved through the use multivariate mathematical techniques, such as PLS, in the deconvolution of the time curve. Calibration models linking the time dependency of the evolution of the $SO_2$ concentration may be constructed by monitoring this evolution in samples having known concentrations and then applied to the deconvolution of the curves from samples with unknown concentrations using known chemometric techniques.

Figure 2:
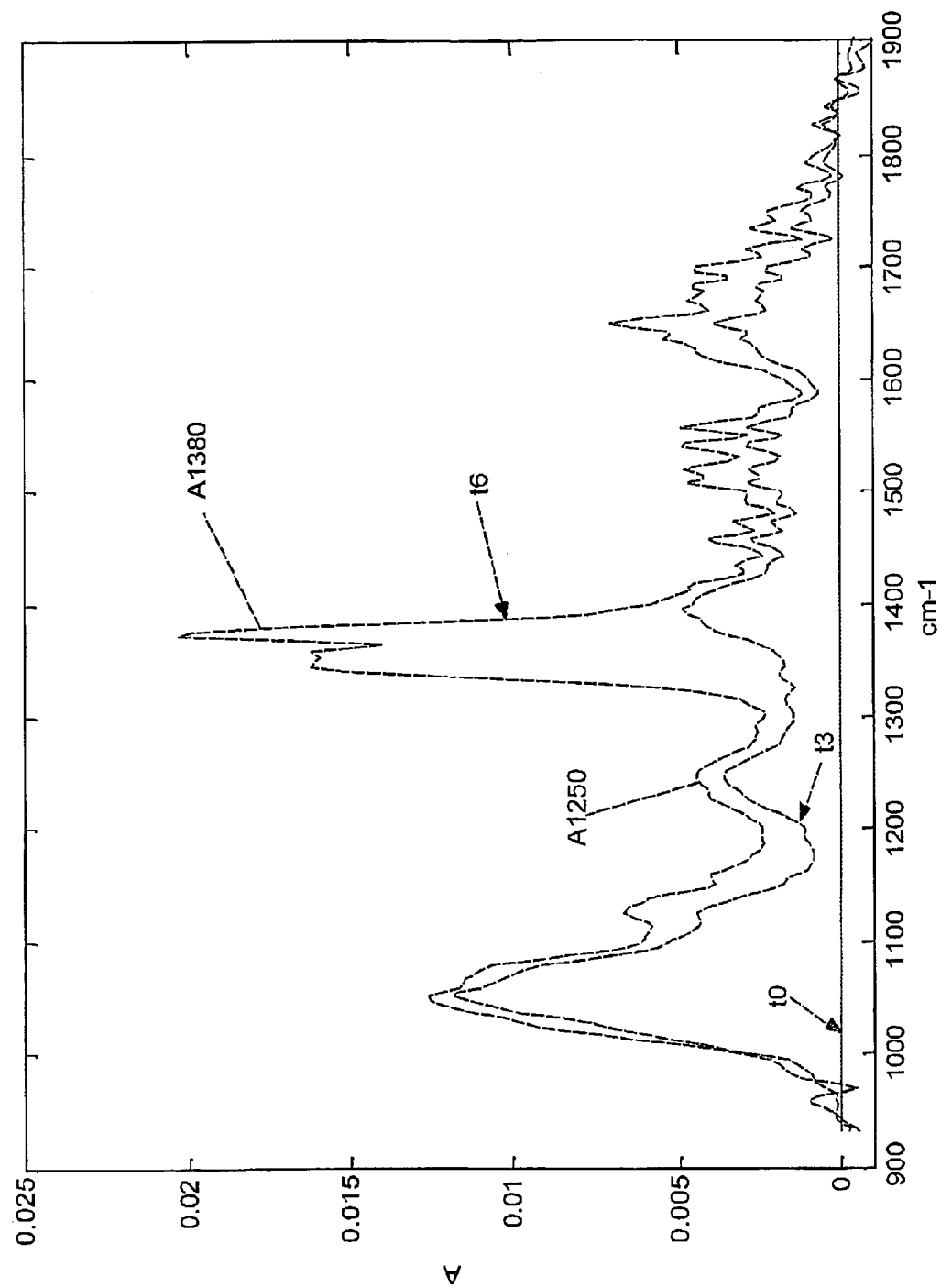
FIG. 2 illustrates the evolution over time of infrared absorption spectra generated by the embodiment of FIG. 1.

Referring now to FIG. 2, representative absorption spectra generated at different times during the operation of the optical measurement instrumentation 4 are illustrated in a plot of absorption intensity (A) against wavelength in $cm^{-1}$. These represent spectra that have been corrected for spectral artefacts unrelated to the absorption by the gas. This is achieved through a subtraction of a base-line spectrum obtained at time t0. An absorption peak ($A_{1250}$) at around 1250 $cm^{-1}$ is related directly to ethanol and a peak ($A_{1380}$) at around 1380 $cm^{-1}$ is related primarily to $SO_2$. The spectrum designated t0 in FIG. 2 is the corrected base-line spectrum, as it is corrected by subtraction of itself then the result is the straight line illustrated. The spectrum designated t3 is the corrected background spectrum and that spectrum designated t6 is a corrected measurement spectrum. These spectra illustrate how absorption intensities of these bands evolve with time t (where t0<t3<t6) and the appearance of the high absorption at 1380 $cm^{-1}$ can be directly associated with the liberation of $SO_2$.

Figure 3:
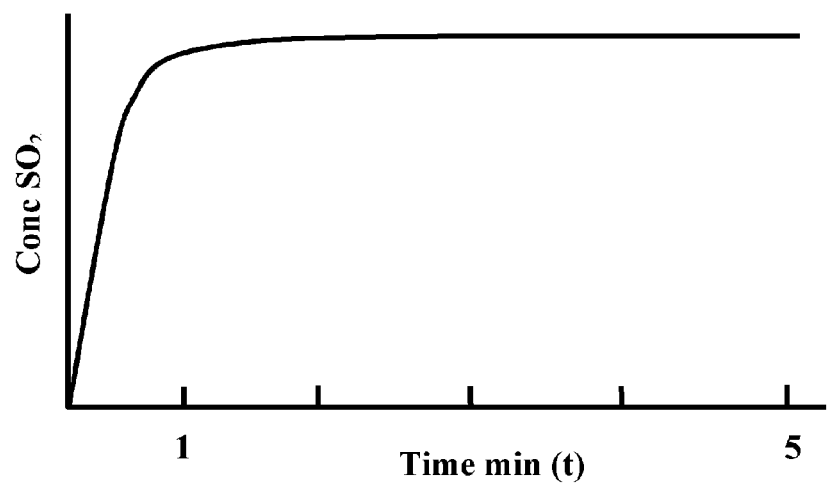
FIG. 3 illustrates the time dependent evolution of $SO_2$ in a liquid sample containing only free $SO_2$.

The evolution with time of the concentration of $SO_2$ for a sample containing only free $SO_2$ is illustrated in FIG. 3. Here the signal processor 30 is operated to determine, using a suitable calibration model, the concentration of $SO_2$ from each of a plurality of infrared absorbance spectra similar to that of FIG. 2, obtained at different times during acid hydrolysis by the measurement instrumentation 4. As can be seen, and as discussed previously, the free $SO_2$ evolves to equilibrium relatively quickly with equilibrium being established after around 1 minute.

Figure 4:
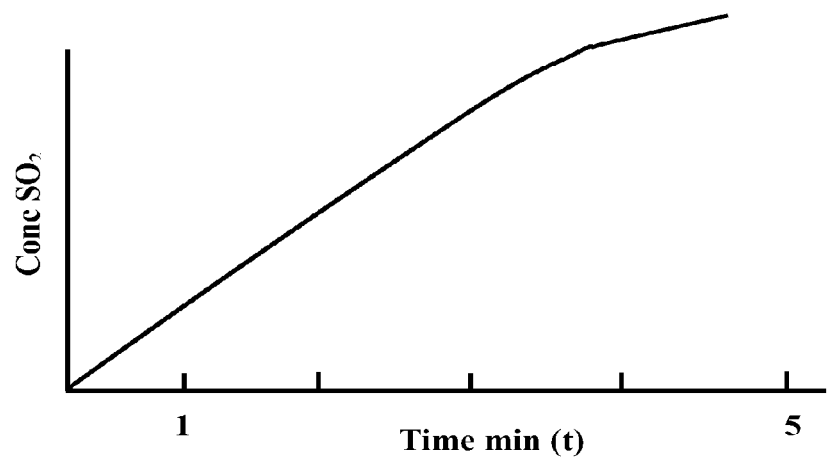
FIG. 4 illustrates the time dependent evolution of $SO_2$ in a liquid sample containing only bound $SO_2$.

The evolution with time of the concentration of $SO_2$ for a sample containing only bound $SO_2$ is illustrated in FIG. 4. Again, the signal processor 30 is operated to determine, using the same calibration model, the concentration of $SO_2$ from each of a plurality of infrared absorbance spectra similar to that of FIG. 2, obtained at different times during acid hydrolysis by the measurement instrumentation 4. As can be seen, and as discussed previously, the bound $SO_2$ evolves to equilibrium relatively slowly and equilibrium has not been reached even after 5 minutes.

Figure 5:
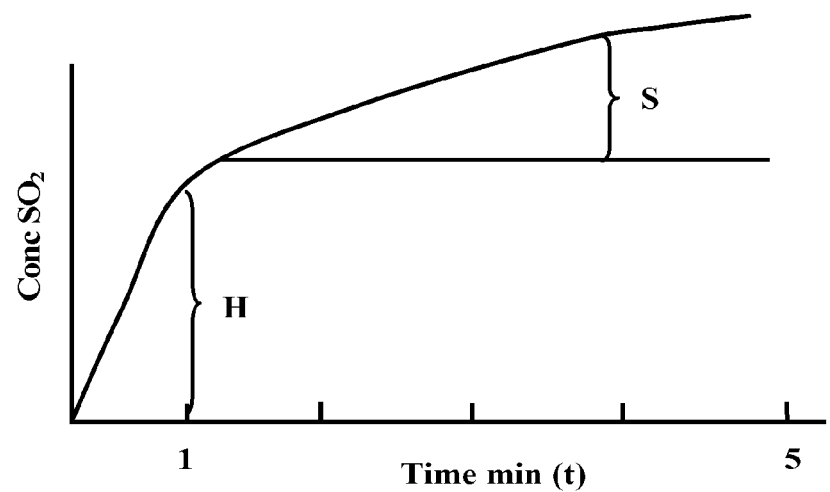
FIG. 5 illustrates the time dependent evolution of $SO_2$ in a liquid sample containing both free and bound $SO_2$.

The evolution with time of the concentration of $SO_2$ in a wine sample is illustrated in FIG. 5 and is shown to be a combination of both the free and the bound curves exemplified in FIGS. 3 and 4 respectively. Analysis of this curve based on a measure of the height (H) in the initial stages and the slope (S) in the later stages of concentration evolution allows for a deconvolution into a concentration in the liquid sample of free $SO_2$ and of bound $SO_2$ respectively. The relationships between H and S and the amounts of $SO_2$ present in the sample may, in one embodiment, be obtained empirically by monitoring H and S after each of a plurality of additions of known amounts of $SO_2$ to the sample. Total $SO_2$ may be simply calculated as the sum of the free and the bound $SO_2$.

Alternatively other chemometric models may be applied in the deconvolution of the curve which results in a direct measure of free and total $SO_2$ concentrations in the liquid sample from which a concentration of the bound $SO_2$ may be deduced if required.

In the further embodiment in which alcohol and sugar concentrations are measured, preferably using the same FTIR detection element 28, the free $SO_2$ concentration value obtained according to the present invention may be used, together with a measure of the pH value, in a known manner to calculate molecular $SO_2$, for example as provided for in the Compendium of International Methods of Analysis-OIV Edition 2011 Vol. 2, Reference MA-AS323-04C where the amount of molecular $SO_2$ (M) is given by:

$$M = X \cdot C \qquad (1)$$

Where C=the free $SO_2$ concentration in mg/L; and X=molecular $SO_2$ as a % of free $SO_2$.

X depends, inter alia, on pH of the wine and its alcohol content and is provided as a look-up table in the referenced publication. This look-up table could be made electronically accessible to the signal processor (30) and used therein to evaluate M using the equation (1).

It will be appreciated that the actual amount of $SO_2$ present in the headspace gas need not be directly determined rather, the development (for example of height and/or of area) over time of an absorption peak known to be associated with the amount of $SO_2$ may be employed to establish the necessary measure of the time dependent concentration variation. It will also be appreciated that other $SO_2$ detectors may be employed to establish its concentration in the headspace gas without departing from the invention as claimed.

The invention claimed is:

1. A method of determining both free and total sulphur dioxide ($SO_2$) in a liquid sample, comprising:
    performing a single hydrolysis reaction of the liquid sample at a temperature above 60° C.;
    monitoring, via a measurement instrument, a temporal evolution of $SO_2$ in headspace gas during the single hydrolysis reaction to establish a measure of a time dependent concentration variation accessible to a signal processor; and
    deconvoluting the established measure of the time dependent concentration variation in the signal processor, the signal processor configured to deconvolute the established measure of the time dependent concentration variation to determine a concentration of the free $SO_2$ based on the single hydrolysis reaction performed at the temperature above 60° C. and a concentration of the total $SO_2$ the liquid sample based on the single hydrolysis reaction performed at the temperature above 60° C.

2. The method as claimed in claim 1, wherein the monitoring the temporal evolution comprises detecting wavelength dependent absorbance values of the headspace gas at one or more wavelengths responsive to changes in $SO_2$ at a plurality of times during the single hydrolysis reaction.

3. The method as claimed in claim 1, wherein the deconvoluting the established measure of the time dependent concentration variation includes subjecting the time dependent concentration variation to a multivariate statistical analysis.

4. The method as claimed in claim 1, wherein the deconvoluting the established measure of the time dependent concentration variation includes subjecting the time dependent concentration variation at longer times to a slope analysis and subjecting the time dependent concentration variation at shorter times to a height analysis.

5. The method as claimed in claim 2, further comprising:
    re-circulating the headspace gas through the liquid sample at least once during the monitoring of the temporal evolution.

6. A system for the determination of free and total $SO_2$ in a liquid beverage product sample, comprising:
    a sample container having a volume sufficient to provide a headspace above the liquid beverage product sample into which a gas can pass;
    a gas flow system configured to extract the gas from the headspace;
    a measurement system configured to monitor a time dependent evolution of $SO_2$ in the gas from the gas flow system;
    a dosing apparatus fluidly connected to the sample container to supply a hydrolysis reagent thereto;
    a heater unit configured to supply thermal radiation into the sample container to elevate a temperature of the liquid beverage product sample therein to above 60° C. to facilitate a single hydrolysis reaction; and
    a signal processor configured to deconvolute the monitored time dependent evolution to determine a concentration of the free $SO_2$ based on the single hydrolysis reaction performed at the temperature above 60° C. and a concentration of the total $SO_2$ of the liquid beverage product sample based on the single hydrolysis reaction performed at the temperature above 60° C.

7. The system as claimed in claim 6, wherein the measurement system comprises an infrared detector arranged to monitor an absorption of infrared radiation in the gas from the gas flow system.

8. The system as claimed in claim 7, wherein the measurement system is configured to monitor an infrared absorption in the liquid beverage product sample.

\* \* \* \* \*